(12) United States Patent
Gibson et al.

(10) Patent No.: US 8,563,611 B2
(45) Date of Patent: Oct. 22, 2013

(54) METHODS AND COMPOSITIONS FOR PROMOTING THE RESPIRATORY DEVELOPMENT OF AN INFANT

(75) Inventors: Robert Gibson, Port Willunga (AU); Maria Makrides, Norwood (AU)

(73) Assignee: Women's & Children's Health Research Institute, North Adelaide, SA (AU)

( * ) Notice: Subject to any disclaimer, the term of this patent is extended or adjusted under 35 U.S.C. 154(b) by 106 days.

(21) Appl. No.: 13/416,557

(22) Filed: Mar. 9, 2012

(65) Prior Publication Data

US 2012/0238626 A1    Sep. 20, 2012

Related U.S. Application Data

(60) Provisional application No. 61/453,598, filed on Mar. 17, 2011.

(51) Int. Cl.
*A61K 31/202* (2006.01)
*A61P 37/08* (2006.01)

(52) U.S. Cl.
USPC ............................................. 514/560

(58) Field of Classification Search
USPC ............................................. 514/560
See application file for complete search history.

(56) References Cited

U.S. PATENT DOCUMENTS

| | | | |
|---|---|---|---|
| 7,211,418 B2 * | 5/2007 | Metz et al | 435/134 |
| 8,277,835 B2 * | 10/2012 | Boehm et al. | 424/439 |
| 2006/0088574 A1 * | 4/2006 | Manning et al. | 424/439 |
| 2007/0004678 A1 * | 1/2007 | Kohn et al. | 514/78 |

* cited by examiner

*Primary Examiner* — Raymond Henley, III
(74) *Attorney, Agent, or Firm* — Roylance, Abrams, Berdo & Goodman, L.L.P.

(57) ABSTRACT

The present invention relates to methods for promoting respiratory development, reducing the incidence of respiratory distress, bronchopulmonary dysplasia and/or hayfever in an infant by administration of fatty acids and compositions comprising same, wherein the fatty acids are enriched with respect to docosahexaenoic acid (DHA) content.

32 Claims, No Drawings

METHODS AND COMPOSITIONS FOR PROMOTING THE RESPIRATORY DEVELOPMENT OF AN INFANT

CROSS REFERENCE TO RELATED CASES

This application claims priority to U.S. Provisional Application Ser. No. 61/453,598, filed Mar. 17, 2011, which is herein incorporated by reference in its entirety.

TECHNICAL FIELD

The present invention is directed to methods for promoting the respiratory development of an infant by administration of fatty acids and compositions comprising same, wherein the fatty acids are enriched with respect to docosahexaenoic acid content.

BACKGROUND OF THE INVENTION

Preterm infants and in particular infants born prior to 33 weeks gestation typically have poor respiratory and survival outcomes as a consequence of poorly developed respiratory systems. Preterm infants also have an increased risk of developing respiratory distress syndrome and/or bronchopulmonary dysplasia (BPD). The introduction of therapies such as antenatal corticosteroids and exogenous surfactants have improved respiratory and survival outcomes, however respiratory distress syndrome and BPD remain major causes of morbidity and mortality in the preterm infant. Further, some preterm and low birth weight infants are more likely to suffer morbidity from atopic conditions including asthma in later life. There is therefore a need for methods which promote respiratory development and thus minimise the incidence and/or risk of respiratory distress syndrome and/or BPD in preterm infants.

An inadequate nutrient supply in the neonatal period is hypothesized to contribute to the observed poor developmental outcome in preterm infants. The n-3 long chain polyunsaturated fatty acid, docosahexaenoic acid (DHA) is of particular interest in this regard because DHA is known to significantly alter a number of basic properties of cell membranes including permeability, fluidity and interactions with regulatory proteins. One such property includes a modulating effect on the activity of ion channels which may facilitate electrical signalling and cellular communication. The uptake of DHA into the developing fetus is maximised during the final trimester of pregnancy and as a result preterm infants do not receive the DHA in utero that is received by their full term counterparts.

The present inventors have surprisingly discovered that the respiratory development of an infant can be promoted by administration of DHA.

SUMMARY OF THE INVENTION

In an aspect, the present invention provides a method for promoting the respiratory development of an infant, the method comprising administering to the infant an effective amount of DHA.

In another aspect, the present invention provides a method for reducing the incidence of respiratory distress, or bronchopulmonary dysplasia in an infant, the method comprising administering to the infant an effective amount of DHA.

In a further aspect the present invention provides a method for reducing the incidence of hayfever in an infant, the method comprising administering to the infant an effective amount of DHA.

The DHA may be administered in an amount of at least about 30 mg/kg of body weight per day.

The DHA may be administered in an amount of at least about 60 mg/kg of body weight per day.

The DHA may be administered in an amount of at least about 90 mg/kg of body weight per day.

The infant may be a preterm infant.

The infant may be born prior to 33 weeks gestation, or prior to 36 weeks gestation.

The administration may be continued until the infant reaches term corrected age.

The infant may be classified as small for gestational age.

The infant may have a birth weight of less than or equal to about 1250 g.

The administration of DHA may commence within about 24 hours of the birth of the infant.

The administration of DHA may commence at a time when the infant commences enteral feeding.

The administration may be enteral or parenteral administration.

The DHA may be administered to the infant in combination with a source of protein.

The DHA may be administered to the infant in combination with vitamins and/or minerals.

The DHA may be administered to the infant in combination with one or more of the following: human milk, infant formula and human milk fortifier.

The DHA may be administered in the form of an emulsion.

The infant may be a male.

The infant's mother may have been identified as being at risk of giving birth to the infant preterm, or at risk of giving birth to an infant that will be classified as small for gestational age.

In a further aspect, the present invention provides a method for promoting the respiratory development of an infant, the method comprising administration to the infant fatty acids including DHA, wherein the DHA represents about 1% or more of the fatty acids.

In a still further aspect, the present invention provides a method for reducing the incidence of respiratory distress and/or bronchopulmonary dysplasia in an infant, the method comprising administration to the infant of fatty acids including DHA, wherein the DHA represents about 1% or more of the fatty acids.

In a yet still further aspect, the present invention provides a method for reducing the incidence of hayfever in an infant, the method comprising administration to the infant fatty acids including DHA, wherein the DHA represents about 1% or more of the fatty acids.

The DHA may be present in an amount of more than 1% of the fatty acids.

The DHA may present in an amount between more than 1% and about 30% of the fatty acids.

The infant may be a preterm infant.

The infant may be born prior to 33 weeks gestation, or prior to 36 weeks gestation.

The administration of DHA may be continued until the infant reaches term corrected age.

The infant may be classified as small for gestational age.

The infant may have a birth weight of less than or equal to about 1250 g.

The administration of DHA may commence within about 24 hours of the birth of the infant.

The administration of DHA may commence at a time when the infant commences enteral feeding.

The administration may be enteral or parenteral administration.

DHA may be administered to the infant at least once a day.

DHA may be administered to the infant at least three times a day.

DHA may be administered to the infant at least five times a day.

The DHA may be administered to the infant in combination with a source of protein.

The DHA may be administered to the infant in combination with vitamins and/or minerals.

The DHA may be administered to the infant in combination with one or more of the following: human milk, infant formula and human milk fortifier.

The DHA may be administered in the form of an emulsion.

The infant may be male.

The infant's mother may be identified as being at risk of giving birth to the infant preterm, or at risk of giving birth to an infant that will be classified as small for gestational age.

In another aspect, the present invention provides a method for promoting the respiratory development of an infant comprising:
  (i) administering fatty acids including DHA to the infant's mother in an amount sufficient to provide a content of DHA in the breast milk of the infant's mother that is about 1% or more of the total fatty acids present in the breast milk, and
  (ii) feeding the infant with breast milk following step (i).

In another aspect, the present invention provides a method of reducing the incidence of respiratory distress and/or bronchopulmonary dysplasia in an infant comprising the method comprising: (i) administering fatty acids including DHA to the infant's mother in an amount sufficient to provide a content of DHA in the breast milk of the infant's mother that is about 1% or more of the total fatty acids present in the breast milk, and (ii) feeding the infant with breast milk following step (i).

In another aspect, the present invention provides a method for reducing the incidence of hayfever in an infant comprising:
  (i) administering fatty acids including DHA to the infant's mother in an amount sufficient to provide a content of DHA in the breast milk of the infant's mother that is about 1% or more of the total fatty acids present in the breast milk, and
  (ii) feeding the infant with breast milk following step (i).

Step (i) may comprise administering fatty acids including DHA to the infant's mother in an amount and over a time period sufficient to provide a constant DHA content in the breast milk of the infant's mother that is about 1% or more of the total fatty acids present in the breast milk of the infant's mother.

Step (i) may comprise administering fatty acids including DHA to the infant's mother on a daily basis, and wherein the daily dosage of DHA is greater than about 600 mg.

Step (i) may comprise administering fatty acids including DHA to the infant's mother on a daily basis, and wherein the daily dosage of DHA is greater than about 800 mg.

Step (i) may comprise administering fatty acids including DHA to the infant's mother on a daily basis, and wherein the daily dosage of DHA is about 900 mg or greater.

The infant may be a pre-term infant.

The infant may be born prior to 33 weeks gestation, or prior to 36 weeks gestation.

The feeding may be continued until the infant reaches term corrected age.

The infant may be classified as small for gestational age.

The infant may have a birth weight of less than or equal to about 1250 g.

The feeding may commence within about 24 hours of the birth of the infant.

Step (ii) may be commenced about 1 week after commencement of step (i).

The feeding may be carried out at least once a day.

The feeding may be carried out at least three times a day.

The feeding may be carried out at least five times a day.

The infant may be a male.

In another aspect, the present invention provides an infant formula comprising fatty acids including DHA, wherein the DHA is present in an amount of about 1% or more of the total fatty acid content in the formula.

The formula may be specialised preterm infant formula.

In another aspect, the present invention provides a composition when used for promoting respiratory development, reducing the incidence of respiratory distress, bronchopulmonary dysplasia and/or hayfever, the composition comprising fatty acids including DHA, wherein the DHA is present in an amount of about 1% or more of the total fatty acid content in the composition.

The composition may be a unit dosage form.

The composition may be adapted for parenteral administration.

The composition may further comprise one or more carriers, diluents and/or adjuvants.

DEFINITIONS

In the context of the present specification, the terms "a" and "an" are used herein to refer to one or to more than one (i.e. to at least one) of the grammatical object of the article. By way of example, "an element" means one element or more than one element.

In the context of the present specification, the term "comprising" means "including principally but not necessarily solely". Furthermore, variations of the word "comprising", such as "comprise" and "comprises", have correspondingly varied meanings.

In the context of this specification, the term "about" is understood to refer to a range of numbers that a person of skill in the art would consider equivalent to the recited value in the context of achieving the same function or result.

In the context of this specification reference to "x % of the total fatty acid content of the composition" or "x % of the total fatty acid content of the formula" or "x % of the total fatty acid content of the mixture" and the like means x % by weight of the total fatty acid content of the composition, formula or mixture.

In the context of this specification, the term "respiratory development" generally refers to growth of the respiratory tract and respiratory system, the ability of the infant to ventilate the lungs and the extent of gas exchange. Respiratory development may be assessed by any suitable means and/or criteria. For example, assessment may be biochemical, clinical and/or histological. The assessment may comprise measuring the requirement for oxygen at a predetermined period of time after birth, for example a term corrected age of 36 weeks.

In the context of the present specification, the term "term corrected age" refers to the age of a preterm infant calculated from the expected date of delivery. The "term corrected age" is thus calculated by subtracting the number of weeks the preterm infant was born before 40 weeks of gestation (in the case of a human infant) from the chronological age. For example a preterm infant born at 28 weeks gestation (3 months premature) with a chronological age of 24 months will have a "term corrected age" of 21 months (24 months chronological age minus 3 months (the number of months premature)).

In the context of this specification, the term "infant" means a being that is less than 24 months of age, and is not limited to a human. The term "infant" is therefore to be construed as encompassing animals, and in particular mammals, including placental mammals, monotremes and marsupials.

In the context of this specification, the term "preterm infant" as it relates to a human being means an infant that is born prior to 37 weeks gestation.

In the context of this specification, the term "preterm infant" as it relates to a non-human being means an infant that is born after the period of viability, but before full term.

In the context of this specification, the term "small for gestational age" means an infant whose birth weight lies below the tenth percentile for that gestational age.

In the context of the present specification, the term "specialised preterm infant formula" means an infant formula intended for administration to preterm infants only comprising selected ingredients so as to satisfy the unique nutritional requirements of preterm infants.

In the context of this specification, the terms "infant formula" and "infant formulas" include formulas that are intended as breast milk replacements or supplements and also milk fortifiers.

DETAILED DESCRIPTION OF THE INVENTION

As exemplified herein, the administration of DHA and fatty acids as described in accordance with the present invention has been shown to have a positive effect on a number of indicators of respiratory development as assessed clinically for example by the need for supplementary oxygen and/or breathing assistance such as continuous positive airway pressure or the use of an endotracheal tube. Accordingly, particular embodiments of the invention relate to methods of promoting respiratory development. In addition, as also exemplified herein the administration of DHA and fatty acids as described is shown to reduce a number of clinical manifestations of allergy, including hayfever. Thus, methods of the invention also find application in the treatment or prevention of allergic conditions such as hayfever.

In one aspect, the present invention relates to a method for promoting the respiratory development of an infant, the method comprising administering to the infant an effective amount of DHA.

In another aspect, the present invention relates to a method for promoting the respiratory development of an infant, the method comprising administration to the infant fatty acids including DHA, wherein the DHA represents about 1% or more of the fatty acids.

In another aspect, the present invention provides a method for reducing the incidence of respiratory distress, bronchopulmonary dysplasia and/or hayfever in an infant. The methods typically comprise administration to the infant of fatty acids including DHA, wherein the DHA represents about 1% or more of the fatty acids.

The methods of the invention promote respiratory development in infants. A promotion of respiratory development may be manifest by improvements in one or more measures of respiratory development such as the need for supplementary oxygen the extent of gas exchange and/or the need for breathing assistance. Those skilled in the art will also appreciate that promoting respiratory development may comprise preventing or treating respiratory or developmental disorders or conditions, for example infections and conditions such as asthma.

In one embodiment, the method may comprise administering to the infant DHA in an amount of at least 30 mg/kg of body weight per day, at least 32 mg/kg of body weight per day, at least 34 mg/kg of body weight per day, at least 36 mg/kg of body weight per day, at least 38 mg/kg of body weight per day, at least 40 mg/kg of body weight per day, at least 42 mg/kg of body weight per day, at least 44 mg/kg of body weight per day, at least 46 mg/kg of body weight per day, at least 48 mg/kg of body weight per day, at least 50 mg/kg of body weight per day, at least 52 mg/kg of body weight per day, at least 54 mg/kg of body weight per day, at least 56 mg/kg of body weight per day, at least 58 mg/kg of body weight per day, at least 60 mg/kg of body weight per day, at least 62 mg/kg of body weight per day, at least 64 mg/kg of body weight per day, at least 66 mg/kg of body weight per day, at least 68 mg/kg of body weight per day, at least 70 mg/kg of body weight per day, at least 72 mg/kg of body weight per day, at least 74 mg/kg of body weight per day, at least 76 mg/kg of body weight per day, at least 78 mg/kg of body weight per day, at least 80 mg/kg of body weight per day, at least 82 mg/kg of body weight per day, at least 84 mg/kg of body weight per day, at least 86 mg/kg of body weight per day, at least 88 mg/kg of body weight per day, at least 90 mg/kg of body weight per day, at least 92 mg/kg of body weight per day, at least 94 mg/kg of body weight per day, at least 96 mg/kg of body weight per day, at least 98 mg/kg of body weight per day, at least 100 mg/kg of body weight per day, at least 102 mg/kg of body weight per day, at least 104 mg/kg of body weight per day, at least 106 mg/kg of body weight per day, at least 108 mg/kg of body weight per day, or at least 110 mg/kg of body weight per day.

In another embodiment, the method may comprise administering to the infant DHA in an amount between about 30 mg/kg of body weight per day and about 500 mg/kg of body weight per day, or between about 32 mg/kg of body weight per day and about 500 mg/kg of body weight per day, or between about 34 mg/kg of body weight per day and about 500 mg/kg of body weight per day, or between about 36 mg/kg of body weight per day and about 500 mg/kg of body weight per day, or between about 38 mg/kg of body weight per day and about 500 mg/kg of body weight per day, or between about 40 mg/kg of body weight per day and about 500 mg/kg of body weight per day, or between about 42 mg/kg of body weight per day and about 500 mg/kg of body weight per day, or between about 44 mg/kg of body weight per day and about 500 mg/kg of body weight per day, or between about 46 mg/kg of body weight per day and about 500 mg/kg of body weight per day, or between about 48 mg/kg of body weight per day and about 500 mg/kg of body weight per day, or between about 50 mg/kg of body weight per day and about 500 mg/kg of body weight per day, or between about 52 mg/kg of body weight per day and about 500 mg/kg of body weight per day, or between about 54 mg/kg of body weight per day and about 500 mg/kg of body weight per day, or between about 56 mg/kg of body weight per day and about 500 mg/kg of body weight per day, or between about 58 mg/kg of body weight per day and about 500 mg/kg of body weight per day, or between about 60 mg/kg of body weight per day and about 500 mg/kg of body weight per day, or between about 62 mg/kg of body weight per day and about 500 mg/kg of body weight per day, or between about 64 mg/kg of body weight per day and about 500 mg/kg of body weight per day, or between about 66 mg/kg of body weight per day and about 500 mg/kg of body weight per day, or between about 68 mg/kg of body weight per day and about 500 mg/kg of body weight per day, or between about 70 mg/kg of body weight per day and about 500 mg/kg of body weight per day, or between about 72 mg/kg of body weight per day and about 500 mg/kg of body weight per day, or between about 74 mg/kg of body weight per day and about 500 mg/kg of body weight per day, or between about 76 mg/kg of body weight per day and about 500 mg/kg of body weight per day, or between about 78 mg/kg of body weight per day and about 500 mg/kg of body weight per day, or between about 80 mg/kg of body weight per day and about 500 mg/kg of body weight per day, or between about 82 mg/kg of body weight per day and about 500 mg/kg of body weight per day, or between about 84 mg/kg of body weight per day and about 500 mg/kg of body weight per day, or between about 86 mg/kg of body weight per day and about 500 mg/kg of body weight per day, or between about 88 mg/kg of body weight per day and about 500 mg/kg of body weight per day, or between about 90 mg/kg of body weight per day and about 500 mg/kg of body weight per day, or between about 92 mg/kg of body weight per day and about 500 mg/kg of body weight per day, or between about 94 mg/kg of body weight per day and about 500 mg/kg of body weight per day, or between about 96 mg/kg of body weight per day and about 500 mg/kg of body weight per day, or between about 98 mg/kg of body weight per day and about 500 mg/kg of body weight per day, or between about 100 mg/kg of body weight per day and about 500 mg/kg of body weight per day, or between about 30 mg/kg of body weight per day and about 300 mg/kg of body weight per day, or between about 35 mg/kg of body weight per day and about 300 mg/kg of body weight per day, or between about 40 mg/kg of body weight per day and about 300 mg/kg of body weight per day, or between about 45 mg/kg of body weight per day and about 300 mg/kg of body weight per day, or between about 50 mg/kg of body weight per day and about 300 mg/kg of body weight per day, or between about 55 mg/kg of body weight per day and about 300 mg/kg of body weight per day, or between about 60 mg/kg of body weight per day and about 300 mg/kg of body weight per day, or between about 65 mg/kg of body weight per day and about 300 mg/kg of body weight per day, or between about 70 mg/kg of body weight per day and about 300 mg/kg of body weight per day, or between about 75 mg/kg of body weight per day and about 300 mg/kg of body weight per day, or between about 80 mg/kg of body weight per day and about 300 mg/kg of body weight per day, or between about 85 mg/kg of body weight per day and about 300 mg/kg of body weight per day, or between about 90 mg/kg of body weight per day and about 300 mg/kg of body weight per day, or between about 95 mg/kg of body weight per day and about 300 mg/kg of body weight per day, or between about 100 mg/kg of body weight per day and about 300 mg/kg of body weight per day, or between about 30 mg/kg of body weight per day and about 200 mg/kg of body weight per day, or between about 40 mg/kg of body weight per day and about 200 mg/kg of body weight per day, or between about 50 mg/kg of body weight per day and about 200 mg/kg of body weight per day, or between about 60 mg/kg of body weight per day and about 200 mg/kg of body weight per day, or between about 70 mg/kg of body weight per day and about 200 mg/kg of body weight per day, or between about 80 mg/kg of body weight per day and about 200 mg/kg of body weight per day, or between about 90 mg/kg of body weight per day and about 200 mg/kg of body weight per day, between about 60 mg/kg of body weight per day and about 180 mg/kg of body weight per day, between about 60 mg/kg of body weight per day and about 150 mg/kg of body weight per day, or between about 60 mg/kg of body weight per day and about 120 mg/kg of body weight per day.

In another embodiment, the method may comprise administration to the infant of DHA in an amount of about 30, 40, 50, 60, 70, 80, 90, 100, 110, 120, 130, 140, 150, 160, 170, 180, 190, 200, 210, 220, 230, 240, 250, 260, 270, 280, 290 or 300 mg/kg of body weight per day.

The DHA may represent about 1.05% or more, about 1.1% or more, about 1.2% or more, about 1.3% or more, about 1.4% or more, about 1.5% or more, about 1.6% or more, about 1.7% or more, about 1.8% or more, about 1.9% or more, about 2.0% or more, about 2.1% or more, about 2.2% or more, about 2.3% or more, about 2.4% or more, about 2.5% or more, about 2.6% or more, about 2.7% or more, about 2.8% or more, about 2.9% or more, about 3.0% or more, about 3.1% or more, about 3.2% or more, about 3.3% or more, about 3.4% or more, about 3.5% or more, about 3.6% or more, about 3.7% or more, about 3.8% or more, about 3.9% or more, about 4.0% or more, about 4.1% or more, about 4.2% or more, about 4.3% or more, about 4.4% or more, about 4.5% or more, about 4.6% or more, about 4.7% or more, about 4.8% or more, about 4.9% or more, or about 5.0% or more of the fatty acids.

The DHA may represent between more than 1% and about 80%, or between more than 1% and about 70%, or between more than 1% and about 60%, or between more than 1% and about 50%, or between more than 1% and about 40%, or between more than 1% and about 30%, or between more than 1% and about 20%, or between more than 1% and about 15%, or between more than 1% and about 10%, or between more than 1% and about 8%, or between more than 1% and about 6%, or between more than 1% and about 5%, or between more than 1% and about 4%, or between more than 1% and about 3%, or between more than 1% and about 2%, of the fatty acids.

The infant may be a preterm infant. In an alternative embodiment the infant may be an infant classified as small for gestational age. Infants that are classified as small for gestational age are typically growth restricted in utero and hence may not have received an adequate supply of DHA. Such infants may therefore derive significant benefit from the methods of the present invention.

The preterm infant may be born prior to 37 weeks gestation, or prior to 36 weeks gestation, or prior to 35 weeks gestation, or prior to 34 weeks gestation, or prior to 33 weeks gestation, or prior to 32 weeks gestation, or prior to 31 weeks gestation, or prior to 30 weeks gestation, or prior to 29 weeks gestation, or prior to 28 weeks gestation, or prior to 27 weeks gestation, or prior to 26 weeks gestation, or prior to 25 weeks gestation, or prior to 24 weeks gestation, or prior to 23 weeks gestation.

The methods and compositions described herein find particular application in relation to infant mammals, for example infant humans. However those skilled in the art will appreciate that the scope of the invention is not so limited and that the compositions and formulas described herein may be administered to infants of any species for the purposes of nutrition and promoting respiratory development, such as in laboratory animals, domestic pets, livestock, the young of stud animals and in rare or endangered species, for example as part of conservation measures in zoological parks and gardens.

The DHA may be administered to the infant via an enteral route or a parenteral route depending on the chronological age of the infant, general health of the infant and whether the infant has commenced enteral feeding. Where the infant has not yet commenced enteral feeding the DHA may be administered parenterally, for example intravenously. Where the infant has commenced enteral feeding the DHA may be administered enterally, for example orally. The method of enteral administration selected will often depend on chronological age, birth weight and the clinical condition of the infant. Typically the route of enteral administration is determined by the infant's ability to co-ordinate sucking, swallowing and breathing. Infants who are less mature, weak or suffering from an illness may require enteral administration via a tube or possibly nasogastrically or orogastrically.

Administration of DHA may commence as soon as possible after the birth of the infant. For example, administration may commence within about 24 hours of the birth of the infant, or within about 12 hours of the birth of the infant, or within about 10 hours of the birth of the infant, or within about 8 hours of the birth of the infant, or within about 6 hours of the birth of the infant, or within about 5 hours of the birth of the infant, or within about 4 hours of the birth of the infant, or within about 3 hours of the birth of the infant, or within about 2 hours of the birth of the infant, or within about 1 hour of the birth of the infant.

In another embodiment, administration to the infant may commence at a time when the infant commences enteral feeding. For example, DHA may be administered within about 24 hours, or within about 12 hours, or within about 8 hours, or within about 4 hours, or within about 2 hours of the infant commencing enteral feeding. In an alternative embodiment administration of DHA may commence simultaneously when the infant commences enteral feeding.

The commencement of DHA administration may be determined on a case-by-case basis and could depend on a number of factors including for example the number of weeks gestation and the general health of the infant post birth.

Where the infant is a preterm infant administration may continue until the infant reaches term corrected age. For example, if the infant is born at 32 weeks gestation administration of DHA may be continued until the infant reaches what would have been full term, i.e. between 37 and 40 weeks gestation, or in other words until the infant reaches a chronological age of between 5 and 8 weeks. Alternatively, if desired, termination of administration may occur at anytime prior to the infant reaching term corrected age.

In alternative embodiments DHA may be administered prior to and beyond term corrected age, for example prior to, and up to 24 months after, term corrected age; or prior to, and up to 18 months after, term corrected age; or prior to, and up to 12 months after, term corrected age; or prior to, and up to 6 months after, term corrected age.

Where the infant is a full term infant and classified as small for gestational age, administration may also commence at a time when the infant commences enteral feeding and may continue for up to 24 months after birth, or up to 18 months after birth, or up to 12 months after birth, or up to 9 months after birth, or up to 6 months after birth, or up to 3 months after birth.

Fatty acids administered in accordance with methods described herein may be administered as part of a composition. Such compositions may take a number of forms that are well known to those skilled in the art including tablets, capsules, caplets, powders, solutions, suspensions and emulsions. The form of the composition is not critical to the invention as long as the infant receives the required amount of DHA. The form of the composition will depend on the intended route of administration. Those skilled in the art will readily appreciate that a number of suitable processes and techniques exist for the manufacture of compositions suitable for enteral and parenteral administration and that the invention is not limited by reference to any one particular process or technique. The methods may involve administration of the composition to the infant once, twice, three, four, five, six or more times per day.

The compositions may be administered to the infant in combination with a source of protein. Protein sources are well known to those skilled in the art and include milk, whey protein, casein, vegetable protein, animal protein, cereal protein, hydrolysed protein, amino acids, peptides and the like. In the case of humans, the source of protein may be human milk, infant formula, human milk fortifier or combinations thereof. The composition may also be administered to an infant in combination with various vitamins and/or minerals which are commonly given to preterm infants and infants classified as small for gestational age. Examples of such vitamins and minerals include, but are not limited to: vitamin A, B group vitamins (for example vitamins $B_1$, $B_2$, $B_5$, $B_6$, $B_9$ and $B_{12}$), vitamin C, vitamin D, vitamin E, vitamin K, vitamin H, zinc, selenium, calcium, phosphorus, sodium, potassium, chloride, manganese, phosphorus, iodine, copper, iron, magnesium, molybdenum and chromium.

In the methods of the invention the DHA may be administered as part of an infant formula. The compositions used in the method of the second aspect may be commercially available infant formulas (for example formulas intended for administration to preterm infants) that have been supplemented such that DHA is present in an amount of about 1% or more of the total fatty acid content of the formula (presently available infant formulas typically comprise DHA in an amount of about 0.3% of the total fatty acid content). The DHA supplementation may occur during manufacture of the formula or alternatively post manufacture. DHA supplementation during manufacture may be performed by replacing the usual fatty acid source or sources with an alternative fatty acid source having the desired DHA content as a percentage of total fatty acids. Alternatively, purified DHA may simply be added to the formula either during or after manufacture so as to achieve the desired DHA content as a percentage of total fatty acids.

The method of the second aspect may involve administering the DHA-supplemented formula according to the daily dosage regime specified by the manufacturer of the formula so that the infant conveniently receives the specified amount of DHA as a percentage of total fatty acid content at each feed. Suitable infant formulas that may be supplemented and administered in this manner include but are not limited to: S-26 LBW Gold available from Wyeth Nutrition, Baulkham Hills, NSW Australia, Nutriprem available from Nutricia, Macquarie Park, NSW Australia, preterm formulas sold under the trade name Enfamil® by MeadJohnson, Indiana, USA, and preNAN® available from Nestle Australia Ltd, Rhodes, NSW Australia.

In an alternative embodiment, the method of the second aspect may involve the use of a DHA-supplemented commercial human milk fortifier which may be intended for administration to preterm infants and which comprises an amount of DHA such that when the fortifier is admixed with an appropriate amount of breast milk, the amount of DHA in the resulting mixture is about 1% or more of the total fatty acid content of the mixture. Typically the amount of DHA added to the human milk fortifier would be calculated on the assumption that mothers consume a minimal amount of DHA-containing products so as to ensure that when the human milk fortifier is added to different breast milks having a range of different DHA contents, the amount of DHA in the resultant mixtures will always be about 1% or more of the total fatty acid content of the mixture. For example, the average amount of DHA as a percentage of total fatty acids in the milk of mothers consuming a typical western diet is less than 0.3%. Accordingly, the amount of DHA present in the DHA-supplemented commercial human milk fortifier would be an amount sufficient to increase this percentage to about 1% or more when admixed with an appropriate amount of breast milk. Suitable commercial human milk fortifiers that may be supplemented and administered in the manner described include but are not limited to: products sold under the trade name Similac® by Abbott Nutrition, Illinois USA, fortifiers sold under the trade name Enfamil® by MeadJohnson, Indiana, USA, S-26 HMF available from Wyeth Nutrition, Baulkham Hills, NSW Australia, and FM-85 available from Nestle Australia Ltd, Rhodes, NSW Australia.

The method may involve administration to the infant of purified DHA, DHA that is present as part of a mixture of fatty acids or any composition comprising DHA (for example infant formulas and human milk fortifiers), so long as the daily dosage of DHA received by the infant is within the dosage regimes described herein.

The source of DHA in the methods, compositions and formulas described herein may be any source known in the art, including plants, marine organisms, algae, bacteria and fungi. The plants, marine organisms, algae, bacteria and fungi may be genetically modified or non-genetically modified. Marine organisms that are a source of DHA include, but are not limited to: crustaceans such as krill, molluscs such as oysters, and fish such as salmon, trout, sardines, tuna, mackerel, sea bass, menhaden, herring, pilchards, kipper, eel or whitebait. Algal sources of DHA include dinoflagellates such as *Crypthecodinium* spp, particularly *C. cohnii* and *Isochrysis* spp such as *I. galbana*. Fungal sources of DHA include thraustochytrid fungi such as *Thraustochytrium* spp and *Schizochytrium* spp, for example *T. aureum, T. roseum, T. motivum, T. multirudimentale* and *S. aggregatum*. Another example of a fungal source of DHA is *Entomophora exitalis*. Bacterial sources of DHA include *Vibrio* spp such as *Vibrio* sp T3615, *Vibrio* sp T5710 and *V. marinus*. Those skilled in the art will understand that the DHA to be used in the methods, compositions and formulas described herein may be derived from any suitable source and is not limited the named sources above.

The DHA may be present in a purified form and/or in the form of an extract from a suitable source. The DHA may be present as a component of fish oil. The fish oil may be obtained from, for example one or more of the following fish: tuna, salmon, trout, menhaden, sea bass, mackerel, sardines, pilchards, herring, kipper, eel, whitebait or any other "fatty fish".

The DHA may be stabilised so as to protect against oxidation and other forms of degradation. The stabilisation may be achieved by encapsulation. Suitable encapsulation methods include, but are not limited to: coatings (including primary, secondary and tertiary), emulsions, coacervation and gels. The DHA may alternatively be stabilised in the form of an emulsion wherein the DHA is either not, or only partially encapsulated.

Preterm human infants and human infants classified as small for gestational age are typically able to consume milk and/or formula in an amount between about 100 mL and 250 mL per kg of body weight per day. Accordingly, embodiments of the invention contemplate the administration to the infant of milk and/or formula in an amount between about 100 mL and 250 mL per kg of body weight per day, wherein the DHA content of the milk or formula is about 1% or more of the total fatty acid content of the milk or formula. The milk and/or formula may be administered to the infant once a day or on multiple occasions depending on the infant's age, general health and feeding regime. As the infant grows, the amount of milk and/or formula can be increased in accordance with the infant's nutritional requirements.

Also contemplated herein are methods for promoting the respiratory development of an infant and for reducing the incidence of respiratory distress, bronchopulmonary dysplasia and/or hayfever in an infant, comprising:
(i) administering fatty acids including DHA to the infant's mother in an amount sufficient to provide a content of DHA in the breast milk of the infant's mother that is about 1% or more of the total fatty acids present in the breast milk, and
(ii) feeding the infant with the breast milk of step (i).

The infant may be a preterm infant or an infant classified as small for gestational age. The feeding may comprise breast feeding or alternatively bottle feeding using expressed milk from the breast of the infant's mother.

Step (i) may comprise administering fatty acids including DHA to the infant's mother in an amount sufficient to provide a content of DHA in the breast milk of the infant's mother that is at least 1%, or at least 1.05%, or at least 1.1%, or at least 1.2%, or at least 1.3%, or at least 1.4%, or at least 1.5%, or at least 1.6%, or at least 1.7%, or at least 1.8%, or at least 1.9%, or at least 2%, or at least 2.1%, or at least 2.2%, or at least 2.3%, or at least 2.4%, or at least 2.5%, or at least 2.6%, or at least 2.7%, or at least 2.8%, or at least 2.9%, or at least 3.0% of the total fatty acids present in the breast milk.

Step (i) may comprise administering fatty acids including DHA to the infant's mother in an amount sufficient to provide a content of DHA in the breast milk of the infant's mother that is between more than 1% and about 20%, or between more than 1.05% and about 20%, or between more than 1.1% and about 20%, or between more than 1% and about 30%, or between more than 1% and about 25%, or between more than 1% and about 15%, or between more than 1% and about 10%, or between about 1.5% and about 20%, or between about 1.5% and about 15%, or between about 1.5% and about 10%, or between about 1.5% and about 5%, or between about 2% and about 20%, or between about 2% and about 15%, or between about 2% and about 10%, of the total fatty acids present in the breast milk.

Step (i) may comprise administering fatty acids including DHA to the infant's mother in an amount and over a time period sufficient to provide a constant DHA content in the breast milk of the infant's mother that is about 1% or more of the total fatty acids present in the breast milk of the infant's mother. This outcome may be achieved by administering to the infant's mother approximately 600 mg or more of DHA per day. However, in the case of a mother who consumes minimal DHA as part of her diet, the amount of DHA administered on a daily basis may be approximately 900 mg or more. In the case of a mother who consumes a diet rich in DHA, it may be possible to achieve a content of DHA in the breast milk of the infant's mother that is about 1% or more of the total fatty acids present by administering less than 600 mg of DHA per day. Those skilled in the art will be capable of determining the amount of DHA required to be administered to an infant's mother in order to achieve a desired amount of DHA as a percentage of total fatty acids in breast milk by routine trial and experimentation based on the teachings herein.

In one embodiment, the amount of DHA administered to the infant's mother may be between about 600 mg per day and about 4000 mg per day, or between about 600 mg per day and about 3500 mg per day, or between about 600 mg per day and about 3000 mg per day, or between about 600 mg per day and about 2500 mg per day, or between about 600 mg per day and about 2000 mg per day, or between about 600 mg per day and about 1500 mg per day, or between about 600 mg per day and about 1200 mg per day.

The DHA may be administered in multiple unit dosage forms (such as tablets or capsules for example), or alternatively in a single unit dosage form comprising the daily amount of DHA. The DHA may be administered in the form of DHA-rich tuna oil, for example the product sold under the trade name HiDHA® available from Nu-Mega Ingredients, Melbourne Australia. In manipulating the amount of DHA present in the breast milk, the naturally occurring amount of arachidonic acid present (about 0.4% to 0.6%) may not be substantially altered.

Step (ii) may be commenced at any time after step (i). In one embodiment step (ii) commences about 1 week after commencement of step (i) thereby ensuring that the desired amount of DHA in the breast milk has been reached and is essentially constant. Practically however it is likely that the infant's mother will simply commence step (i) whilst continuing the infant's standard feeding regime. Accordingly, the level of DHA in the breast milk being received by the infant will increase and subsequently be maintained at, or above, the desired level.

The method may commence at anytime after the birth of the infant, and in one embodiment within about 24 hours of the birth of the infant. Commencement of the method will of course be dependent on whether the infant is capable of breastfeeding or bottle feeding expressed milk. Where the infant is unable to commence breastfeeding or bottle feeding soon after birth, the method may be commenced once the infant is able to breastfeed or bottle feed successfully.

In another aspect, the present invention relates to an infant formula for promoting respiratory development, reducing the incidence of respiratory distress, bronchopulmonary dysplasia and/or hayfever in an infant, the formula comprising fatty acids including DHA, wherein the DHA is present in an amount of about 1% or more of the total fatty acid content in the formula. The infant formula may be a milk fortifier or formula intended for use as a breast milk replacement or supplement. In preferred embodiments, the infant formula is intended for enteral administration to an infant. For example the formula may be administered orally.

The DHA may be present in the formula in an amount of about 1.05% or more, about 1.1% or more, about 1.2% or more, about 1.3% or more, about 1.4% or more, about 1.5% or more, about 1.6% or more, about 1.7% or more, about 1.8% or more, about 1.9% or more, about 2.0% or more, about 2.1% or more, about 2.2% or more, about 2.3% or more, about 2.4% or more, about 2.5% or more, about 2.6% or more, about 2.7% or more, about 2.8% or more, about 2.9% or more, about 3.0% or more, about 3.1% or more, about 3.2% or more, about 3.3% or more, about 3.4% or more, about 3.5% or more, about 3.6% or more, about 3.7% or more, about 3.8% or more, about 3.9% or more, about 4.0% or more, about 4.1% or more, about 4.2% or more, about 4.3% or more, about 4.4% or more, about 4.5% or more, about 4.6% or more, about 4.7% or more, about 4.8% or more, about 4.9% or more, or about 5.0% or more, of the total fatty acid content of the formula.

In an alternative embodiment, the DHA may be present in the formula in an amount between more than 1% and about 80%, or between more than 1% and about 70%, or between more than 1% and about 60%, or between more than 1% and about 50%, or between more than 1% and about 40%, or between more than 1% and about 30%, or between more than 1% and about 20%, or between more than 1% and about 15%, or between more than 1% and about 10%, or between more than 1% and about 8%, or between more than 1% and about 6%, or between more than 1% and about 5%, or between more than 1% and about 4%, or between more than 1% and about 3%, or between more than 1% and about 2%, of the total fatty acid content of the formulas.

The infant formula in accordance with the invention will typically be nutritionally complete and include standard ingredients that are present in commercially available infant formulas and milk fortifiers, such as fat, protein, carbohydrate, vitamins and minerals. The nutritional composition of the formulas and fortifiers may be adjusted depending on the intended age group to which the formulas and fortifiers are to be administered. For example, in one embodiment the infant formulas are specialised preterm infant formulas and hence include selected ingredients so as to satisfy the unique nutritional requirements of preterm infants. Alternatively, where the formulas and fortifiers are intended to be administered to infants that are older than term corrected age, the nutritional composition may be adjusted to meet the differing nutritional requirements of such infants. The formulas may be in the form of liquids, powders or tablets and may be manufactured according to techniques well known to those skilled in the art.

In one embodiment, the infant formula of the invention may be prepared by supplementing commercially available infant formulas or fortifiers with the desired amount of DHA as described above in connection with the second aspect. Suitable infant formulas that may be supplemented in this manner include, but are not limited to: products sold under the trade name Similac® by Abbott Nutrition, Illinois USA, products sold under the trade name S-26 (for example S-26 LBW Gold and S-26 HMF) available from Wyeth Nutrition, Baulkham Hills, NSW Australia, Nutriprem available from Nutricia, Macquarie Park, NSW Australia, products sold under the trade name Enfamil® by MeadJohnson, Indiana, USA and FM-85 and preNAN®, both available from Nestle Australia Ltd, Rhodes, NSW Australia.

In another aspect, the present invention relates to a composition when used for promoting respiratory development, reducing the incidence of respiratory distress, bronchopulmonary dysplasia and/or hayfever in an infant, the composition comprising fatty acids including DHA, wherein the DHA is present in an amount of about 1% or more of the total fatty acid content in the composition.

The DHA may be present in the composition in an amount of about 1.05% or more, about 1.1% or more, about 1.2% or more, about 1.3% or more, about 1.4% or more, about 1.5% or more, about 1.6% or more, about 1.7% or more, about 1.8% or more, about 1.9% or more, about 2.0% or more, about 2.1% or more, about 2.2% or more, about 2.3% or more, about 2.4% or more, about 2.5% or more, about 2.6% or more, about 2.7% or more, about 2.8% or more, about 2.9% or more, about 3.0% or more, about 3.1% or more, about 3.2% or more, about 3.3% or more, about 3.4% or more, about 3.5% or more, about 3.6% or more, about 3.7% or more, about 3.8% or more, about 3.9% or more, about 4.0% or more, about 4.1% or more, about 4.2% or more, about 4.3% or more, about 4.4% or more, about 4.5% or more, about 4.6% or more, about 4.7% or more, about 4.8% or more, about 4.9% or more, or about 5.0% or more, of the total fatty acid content of the composition.

In an alternative embodiment, the DHA may be present in the composition in an amount between more than 1% and about 80%, or between more than 1% and about 70%, or between more than 1% and about 60%, or between more than 1% and about 50%, or between more than 1% and about 40%, or between more than 1% and about 30%, or between more than 1% and about 20%, or between more than 1% and about 15%, or between more than 1% and about 10%, or between more than 1% and about 8%, or between more than 1% and about 6%, or between more than 1% and about 5%, or between more than 1% and about 4%, or between more than 1% and about 3%, or between more than 1% and about 2%, of the total fatty acid content of the composition.

The composition may comprise one or more acceptable carriers, diluents, adjuvants, emulsifiers, preservatives, and microencapsulating agents known to the person skilled in the art. The carriers, diluents adjuvants, emulsifiers, preservatives, and microencapsulating agents must be "acceptable" in terms of being compatible with the other components of the composition and not deleterious to the recipient thereof. Typically, the carriers, diluents, emulsifiers, preservatives, and microencapsulating agents must be "acceptable" in terms of being suitable for oral consumption by an infant.

Suitable carriers, diluents, adjuvants, emulsifiers, preservatives and microencapsulating agents will depend on the intended route of administration and are well known to those skilled in the art. In one embodiment, the composition may be adapted for parenteral administration. For administration as an injectable solution or suspension non-toxic parenterally acceptable diluents or carriers can include: Ringer's solution, isotonic saline, glucose solution, distilled water and phosphate buffered saline. Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may be a unit dosage form suitable for oral administration, for example a tablet, capsule, caplet, or lozenge. Unit dosage forms may optionally include one or more acceptable excipients, for example ethyl cellulose, cellulose acetate phthalates, mannitol, lactose, starch, magnesium stearate, sodium saccharin, talc, glucose, sucrose, carbonate, and the like.

Examples of acceptable carriers or diluents include demineralised or distilled water, saline solution, vegetable based oils such as peanut oil, safflower oil; olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; cellulose derivatives such as methyl cellulose, ethyl cellulose, carboxymethylcellulose, sodium carboxymethylcellulose, or hydroxypropylmethylcellulose, liquid paraffin, sodium alginate, gum acacia, gum tragacanth, dextrose, sucrose, sorbitol, mannitol, gelatine, lecithin, lower alkylene glycols, for example polyethylene glycol, polypropylene glycol or propylene glycol, or glycerine, fatty acid esters such as isopropyl palmitate, isopropyl myristate or ethyl oleate, polyvinylpyrridone, agar, carrageenan; gum tragacanth or gum acacia, and petroleum jelly. Adjuvants typically include emollients, emulsifiers, thickening agents, preservatives, bactericides and buffering agents.

Compositions of the present invention may be prepared by blending, grinding, homogenising, suspending, dissolving, emulsifying, spray drying, dispersing and/or mixing the ingredients with the selected carrier(s), adjuvant(s) and/or diluent(s). Emulsions for oral administration may further comprise one or more emulsifying agents. Suitable emulsifying agents include natural gums such as guar gum, gum acacia or gum tragacanth. The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It will be appreciated by persons skilled in the art that numerous variations and/or modifications may be made to the invention without departing from the spirit or scope of the invention as broadly described. The present embodiments are therefore to be considered in all respects as illustrative and not restrictive.

The invention will now be described in more detail, by way of illustration only, with respect to the following examples. The examples are intended to serve to illustrate this invention and should not be construed as limiting the generality of the disclosure of the description throughout this specification.

EXAMPLE

Clinical Study

Study Design and Methodology

A multi-centre randomized controlled trial was conducted in 5 Australian perinatal centres. Ethics approval was granted by the local Institutional Review Boards (Human Research Ethics Committees) of each centre. The trial began with a pilot phase at the Women's and Children's Hospital, Adelaide. A central trial coordinator monitored data collection, entry and checking. An independent serious adverse event committee reviewed all deaths.

Infants born <33 weeks were eligible and families were approached by the research nurses within 5 days of their infant receiving any enteral feeds. Infants were excluded if they had major congenital or chromosomal abnormalities, were from a multiple birth where not all live born infants were eligible, or were in other trials of fatty acid supplementation. Lactating mothers in whom tuna oil was contraindicated, for example bleeding disorders or therapy with anticoagulants, were also excluded.

Once written informed consent was obtained, mother-infant pairs were randomly assigned a unique study number through a computer driven telephone randomization service according to an independently generated randomization schedule. Stratification was by centre, birth weight (<1250 g and ≥1250 g) and infant sex. Multiple births were considered a single randomization unit and randomization of twins or triplets was according to the sex and birth weight of the first born infant. Baseline characteristics, including maternal age, infant race as identified by parents, parental education, birth order, parity, gestational age at birth, birth measurements, pregnancy and birth complications, were recorded.

Lactating mothers allocated to the high-DHA group were asked to consume 6×500 mg DHA-rich tuna oil capsules per day in order to achieve a breast milk DHA concentration that was ≈1% of total fatty acids without altering the naturally occurring concentration of arachidonic acid (AA) in breast milk. If supplementary formula was required, infants were given a high-DHA preterm formula (≈1.0% DHA, 0.6% AA). Mothers with infants allocated to the standard DHA group were asked to consume 6×500 mg placebo, soy oil capsules that did not change the fat content or fatty acid composition of their milk. In the event that mothers chose not to breastfeed or could not produce enough breast milk, infants were fed standard preterm infant formula (≈0.35% DHA and 0.6% AA). To facilitate blinding, each treatment group was separately colour coded into two groups. All capsules were similar in size, shape and colour and were donated by Clover Corporation, Sydney, Australia. If formula was required in the pilot phase, two drops of oil from capsules in matching colour coded containers were added to each 90 mL jar of formula. For the remainder of the trial, Mead Johnson Nutritionals, IN, USA, specifically manufactured ready-to-feed preterm formula to trial specifications and packaged the formula according to the colour codes. The intervention continued until infants reached their expected date of delivery (EDD). Infants in the high-DHA group consumed approximately 60 mg/kg of body weight per day of DHA, whereas infants in the standard DHA group consumed approximately 20 mg/kg of body weight per day of DHA. Whilst in hospital, the feeding regimen was under the direction of the infant's clinician and did not interfere with the use of human milk fortifier or supplementary vitamins or minerals. Post-term, breastfeeding mothers were encouraged to continue breastfeeding and those who had weaned to formula were encouraged to use a term formula supplemented with DHA and AA. Parents were reimbursed the difference in cost between unsupplemented term formula and DHA-supplemented term formula.

During the intervention the proportion of parenteral and enteral nutrition, human milk and infant formula intakes, and the frequency of interrupted feeds were documented weekly. Confirmed cases of necrotizing enterocolitis (NEC), sepsis, intra-ventricular hemorrhage (IVH), retinopathy of prematurity (ROP) and oxygen treatment at 36 weeks were also documented. Weight, length and head circumference were assessed at EDD and women who were breastfeeding donated a 5 mL sample of milk to assess the fatty acid composition (Makrides et al. Effect of maternal docosahexaenoic acid (DHA) supplementation on breast milk composition. *Eur J Clin Nutr.* 1996; 50(6): 352-357). At EDD, women were also asked to guess their group allocation.

Data collected included survival to discharge, duration of respiratory support via an endotracheal tube, requirement for postnatal steroid therapy, duration of nasal continuous positive airway pressure treatment, days requiring supplemental oxygen, oxygen requirement at a corrected age of 36 weeks gestation (defined as BPD), total days in the neonatal intensive care unit, and total days in hospital care. Questionnaires were administered to parents at 12 and 18 months follow-up, and these allowed parental reporting of diagnosis or treatment for hay fever, eczema, asthma or food allergy. Requirement for home oxygen after discharge and need for re-admission to hospital were also recorded from parental interview.

All analyses were conducted according to the intention-to-treat principle. The models used to estimate relative risks were generalized estimating equations specifying a binomial distribution and log link. Subgroup analyses were performed by testing for an interaction between treatment and subgroup. For this report, non-imputed data were used in all analyses. All outcomes were adjusted for the potential confounders of infant sex and gestational age at delivery; we provide both unadjusted and adjusted results. The a priori level of significance was $P<0.05$, no adjustment has been made for multiple testing.

Results

A total of 657 infants were enrolled (322 high-DHA diet, 335 standard-DHA diet), and 614 infants (93.5%) completed 18-month follow-up. Whilst there was a high retention rate in the trial, allergy data were incomplete at 12-month and 18-months corrected age, largely because the families who participated in the pilot phase of the trial did not complete the allergy questionnaires; the number of infants for whom data were complete is indicated in Tables 1 to 3. The demographic and clinical characteristics were comparable between the groups. Median duration of treatment was comparable between the high-DHA and standard-DHA groups: 9.4 weeks, interquartile range (IQR) 7.9-11.4 weeks, vs. 9.4 (8.0-11.6) weeks, respectively.

Overall, infants in the high-DHA group showed a trend towards a reduction in BPD, adjusted relative risk 0.77 (95% confidence interval 0.59, 1.02), P=0.07 (Table 4). However, there were significant treatment by BW and treatment by sex interactions indicating differential response to higher DHA treatment by stratification variables. Subgroup analysis demonstrated a significant reduction in oxygen requirement at 36 weeks' in infants with BW<1250 g, RR 0.75 (0.57, 0.98), P=0.04; and in male infants, 0.67 (0.47, 0.96), P=0.03.

There was a reduction in hay fever noted in the high-DHA group at either 12 or 18 months, RR 0.41 (0.18, 0.91), P=0.03 (Table 4). Subgroup analysis of this finding (Table 5) revealed a reduction in hay fever approaching significance in infants with BW≥1250 g, RR 0.29 (0.08, 1.02), P=0.05, and a significant reduction in male infants at 12 months, RR 0.11 (0.01, 0.85), P=0.03, and at either 12 or 18 months, RR 0.15 (0.03, 0.64), P=0.01.

TABLE 1

Baseline Demographic and Clinical Characteristics of Children and their Families

| Characteristic | High-DHA (n = 322) | Standard-DHA (n = 335) |
|---|---|---|
| Recruitment Hospital | | |
| Flinders Medical Centre | 31 (9.6) | 32 (9.6) |
| King Edward Memorial Hospital | 65 (20.2) | 57 (17.0) |
| Royal Brisbane & Women's Hospital | 46 (14.3) | 50 (14.9) |
| Royal Women's Hospital | 61 (18.9) | 63 (18.8) |
| Women's & Children's Hospital | 119 (37.0) | 133 (39.7) |
| Mother's Age at Trial Entry (years) | 29.9 (5.8) | 30.2 (5.4) |
| Mother Completed Secondary Education | 205 (63.7) | 201 (60.1) |
| Father Completed Secondary Education | 172 (53.5) | 188 (56.0) |
| Mother Smoked During Pregnancy | 82 (25.6) | 84 (25.1) |
| Previous PreTerm Births | 51 (15.8) | 58 (17.4) |
| Birth by Caesarean Section | 220 (68.3) | 235 (70.0) |
| Antenatal Steroids Administered | 279 (86.6) | 302 (90.1) |
| Multiple Pregnancy | 98 (30.4) | 123 (36.7) |
| Gestational Age at Birth (weeks) | 30 (27-31) | 30 (27-31) |
| Caucasian | 283 (87.9) | 311 (92.8) |
| Male Sex | 173 (53.7) | 182 (54.3) |
| Birth Weight (g) | 1308 (423) | 1307 (415) |
| Small for gestational age | 61 (18.9) | 62 (18.6) |
| Birth Weight <1250 g | 147 (45.7) | 149 (44.5) |
| Recumbent Length At Birth (cm) | 38.2 (4.0) | 38.1 (4.0) |
| Head Circumference At Birth (cm) | 27.2 (2.8) | 27.3 (2.7) |
| Days of Partial Enteral Feeds Pre-Randomization | 2 (1-4) | 2 (0-3) |
| Infant Age at Randomization (days) | 4 (3-6) | 4 (2-5) |
| Infants Receiving Breast Milk at Trial Entry | 297 (92.2) | 306 (91.3) |

Values are number (%) of babies, mean (sd) or median (interquartile range)

TABLE 2

Secondary Clinical Outcomes

|  | High-DHA | Standard-DHA | Unadjusted Effect (95% CI) | Unadjusted P-value | Adjusted Effect (95% CI) | Adjusted P-value |
|---|---|---|---|---|---|---|
| All | n = 322 | n = 335 |  |  |  |  |
| Death | 9 (2.8) | 9 (2.7) | 1.04 (0.42, 2.59) | 0.93 | 1.09 (0.44, 2.66) | 0.86 |
| Pre-Discharge Death | 9 (2.8) | 6 (1.8) | 1.56 (0.56, 4.34) | 0.39 | 1.66 (0.63, 4.41) | 0.31 |
| Days In NICU | 22 (3-31) | 21 (4-33) | 1.02 (0.82, 1.27) | 0.87 | 1.03 (0.88, 1.20) | 0.75 |
| Days In Hospital Care | 64 (40-80) | 64 (41-80) | 1.01 (0.92, 1.10) | 0.87 | 1.00 (0.95, 1.06) | 0.92 |
| Days On Parenteral Nutrition | 12 (5-15) | 12 (5-14) | 1.06 (0.90, 1.24) | 0.52 | 1.03 (0.92, 1.16) | 0.59 |
| Days Of Intravenous Lipids | 8 (0-12) | 8 (0-10) | 1.06 (0.85, 1.32) | 0.59 | 1.06 (0.87, 1.30) | 0.54 |
| Days Until Full Enteral Feeds | 12 (6-14) | 12 (6-14) | −0.2 (−2.0, 1.6) | 0.82 | −0.2 (−1.0, 0.6) | 0.55 |
| Exclusively Human Milk Fed at EDD | 142 (44.1) | 135 (40.2) | 1.10 (0.87, 1.39) | 0.42 | 1.11 (0.88, 1.40) | 0.39 |
| Feeding Interrupted | 106 (32.9) | 106 (31.6) | 1.04 (0.82, 1.32) | 0.74 | 1.07 (0.87, 1.31) | 0.55 |
| Any NEC | 14 (4.3) | 7 (2.1) | 2.06 (0.83, 5.13) | 0.12 | 2.14 (0.87, 5.22) | 0.10 |
| Bowel Surgery | 12 (3.7) | 9 (2.7) | 1.39 (0.58, 3.33) | 0.46 | 1.45 (0.63, 3.35) | 0.39 |
| Oxygen Treatment at 36 weeks | 60 (18.6) | 84 (25.1) | 0.74 (0.54, 1.02) | 0.07 | 0.76 (0.58, 1.00) | 0.05 |
| Any Intraventricular Haemorrhage | 45 (14.0) | 44 (13.2) | 1.06 (0.71, 1.59) | 0.77 | 1.07 (0.72, 1.58) | 0.73 |
| Severe Intraventricular Haemorrhage[a] | 9 (2.8) | 6 (1.8) | 1.56 (0.56, 4.33) | 0.39 | 1.63 (0.61, 4.33) | 0.33 |
| Any Retinopathy of Prematurity | 74 (23.0) | 73 (21.8) | 1.05 (0.77, 1.45) | 0.74 | 1.09 (0.85, 1.40) | 0.49 |
| Severe Retinopathy of Prematurity[b] | 14 (4.3) | 17 (5.1) | 0.86 (0.42, 1.75) | 0.67 | 0.91 (0.46, 1.80) | 0.79 |
| Any Sepsis | 53 (16.6) | 48 (14.3) | 1.16 (0.79, 1.69) | 0.46 | 1.18 (0.85, 1.65) | 0.32 |
| Postnatal steroids | 30 (9.3) | 34 (10.2) | 0.92 (0.56, 1.51) | 0.73 | 0.96 (0.61, 1.50) | 0.85 |
| Small for gestational age at EDD | 109 (33.8) | 105 (31.4) | 1.08 (0.85, 1.37) | 0.53 | 1.09 (0.86, 1.37) | 0.49 |
| Weight at EDD (g) | 3175 (553) | 3129 (535) | 42 (−118, 203) | 0.60 | 42 (−116, 199) | 0.60 |
| Weight at 18 Months (g) | 11625 (1811) | 11277 (1588) | 201 (−237, 639) | 0.37 | 187 (−250, 623) | 0.40 |
| Length at EDD (cm) | 48.7 (3.3) | 48.4 (3.3) | 0.2 (−0.3, 0.8) | 0.42 | 0.2 (−0.3, 0.8) | 0.45 |
| Length at 18 Months (cm) | 82.8 (5.2) | 81.7 (4.7) | 0.9 (0.2, 1.7) | 0.01 | 0.9 (0.2, 1.6) | 0.01 |
| Head circumference at EDD (cm) | 35.4 (1.8) | 35.4 (1.9) | 0.10 (−0.6, 0.7) | 0.85 | 0.10 (−0.6, 0.7) | 0.85 |
| Head circumference at 18 Months (cm) | 47.6 (2.5) | 47.6 (2.2) | −0.06 (−0.8, 0.7) | 0.86 | −0.05 (−0.8, 0.7) | 0.88 |
| Seizures at 18 months | 7 (2.0) | 17 (5.2) | 0.39 (0.15, 1.04) | 0.06 | 0.39 (0.15, 1.04) | 0.06 |
| Unilateral or bilateral blindness at 18 months | 0 | 1 (0.3) | — | — | — | — |
| Severe hearing loss requiring aids at 18 months | 0 | 1 (0.3) | — | — | — | — |
| Cerebral Palsy at 18 months | 13 (3.9) | 10 (3.0) | 1.31 (0.56, 3.06) | 0.53 | 1.31 (0.56, 3.06) | 0.53 |

Values are number of babies (%) with effect being Relative Risk or mean (interquartile range) with Ratio of Means as effect
Adjusted for GA at delivery and sex. Further adjustment for pilot phase vs multi-centre phase did not alter the results.
[a]Grade 3 or 4
[b]Grade 3 or higher

TABLE 3

Respiratory data

| ALL INFANTS | High-/Standard-DHA Diet, No. | High-DHA Diet, No. (%) or mean (IQR) | Standard-DHA Diet, No. (%) or mean (IQR) | Unadjusted Relative Risk (95% CI) | Unadjusted P-value | Adjusted Relative Risk* (95% CI) | Adjusted P-value |
|---|---|---|---|---|---|---|---|
| Pre-discharge death^ | 322/335 | 9 (2.8) | 6 (1.8) | 1.56 (0.56, 4.34) | 0.39 | 1.66 (0.63, 4.41) | 0.31 |
| Days on endotracheal support | 321/334 | 6.1 (0-5) | 6.8 (0-5) | 0.90 (0.63, 1.29) | 0.58 | 0.88 (0.65, 1.18) | 0.39 |
| Days on CPAP | 321/334 | 9.4 (1-12) | 9.1 (0-10) | 1.02 (0.79, 1.33) | 0.85 | 1.04 (0.83, 1.30) | 0.72 |
| Days requiring oxygen (up to EDD) | 321/334 | 21.6 (1-29) | 25.5 (1-51) | 0.85 (0.67, 1.08) | 0.19 | 0.82 (0.64, 1.06) | 0.13 |
| Oxygen at 36 Weeks^ | 319/334 | 60 (18.8) | 84 (25.1) | 0.75 (0.54, 1.03) | 0.07 | 0.77 (0.59, 1.02) | 0.07 |
| Birth weight < 1250 g | 145/149 | 50 (34.5) | 70 (47.0) | 0.73 (0.55, 0.99) | 0.04 | 0.75 (0.57, 0.98) | 0.04 |
| Birth weight ≥ 1250 g | 174/185 | 10 (5.7) | 14 (7.6) | 0.76 (0.34, 1.70) | 0.50 | 0.81 (0.37, 1.80) | 0.61 |
| Male infants | 171/182 | 32 (18.7) | 51 (28.0) | 0.67 (0.45, 1.00) | 0.05 | 0.67 (0.47, 0.96) | 0.03 |
| Female infants | 148/152 | 28 (18.9) | 33 (21.7) | 0.87 (0.53, 1.42) | 0.58 | 0.94 (0.64, 1.39) | 0.76 |
| Baby discharged home on oxygen | 318/334 | 29 (9.1) | 37 (11.1) | 0.82 (0.51, 1.33) | 0.43 | 0.87 (0.55, 1.36) | 0.54 |
| Days in NICU^ | 321/334 | 21.7 (3-31) | 21.3 (4-33) | 1.02 (0.82, 1.27) | 0.88 | 1.03 (0.88, 1.20) | 0.75 |
| Days in hospital care^ | 319/332 | 64.8 (41-80) | 64.4 (41-80) | 1.01 (0.92, 1.10) | 0.87 | 1.00 (0.95, 1.06) | 0.88 |
| Any re-admission to hospital | 300/313 | 159 (53) | 170 (54.3) | 0.98 (0.83, 1.14) | 0.76 | 0.98 (0.85, 1.14) | 0.81 |
| Postnatal steroids^ | 320/332 | 30 (9.4) | 34 (10.2) | 0.92 (0.56, 1.51) | 0.73 | 0.96 (0.61, 1.51) | 0.86 |

Non-imputed data presented. Abbreviations: DHA, docosahexaenoic acid; IQR, interquartile range; CI, confidence interval; CPAP, continuous positive airway pressure; EDD, expected date of delivery; NICU, neonatal intensive care unit.
*Adjusted for GA at delivery and sex
^Previously reported outcome using multiple imputation for missing data (8). Data presented here is non-imputed; subgroup analysis of oxygen at 36 weeks has not been previously reported.

TABLE 4

Allergy data for all infants

| ALL INFANTS | High-/Standard-DHA Diet, No. | High-DHA Diet, No. (%) | Standard-DHA Diet, No. (%) | Unadjusted Relative Risk (95% CI) | Unadjusted P value | Adjusted Relative Risk* (95% CI) | Adjusted P value |
|---|---|---|---|---|---|---|---|
| Hay fever | | | | | 0.16 | | 0.16 |
| 12 Months | 232/249 | 5 (2.2) | 13 (5.2) | 0.41 (0.15, 1.16) | 0.09 | 0.41 (0.15, 1.16) | 0.09 |
| 18 Months | 292/311 | 7 (2.4) | 10 (3.2) | 0.75 (0.28, 2.00) | 0.56 | 0.75 (0.28, 2.01) | 0.57 |
| Either 12 or 18 months# | 231/244 | 8 (3.5) | 21 (8.6) | 0.40 (0.18, 0.91) | 0.03 | 0.41 (0.18, 0.91) | 0.03 |
| Asthma | | | | | 0.48 | | 0.49 |
| 12 Months | 232/249 | 18 (7.8) | 25 (10.0) | 0.77 (0.42, 1.41) | 0.40 | 0.77 (0.42, 1.40) | 0.39 |
| 18 Months | 292/311 | 41 (14.0) | 46 (14.8) | 0.95 (0.63, 1.43) | 0.80 | 0.96 (0.64, 1.43) | 0.83 |
| Either 12 or 18 months# | 237/252 | 47 (19.8) | 53 (21.0) | 0.94 (0.65, 1.36) | 0.75 | 0.95 (0.66, 1.36) | 0.78 |
| Eczema | | | | | 0.50 | | 0.51 |
| 12 Months | 232/249 | 29 (12.5) | 40 (16.1) | 0.78 (0.49, 1.22) | 0.28 | 0.78 (0.50, 1.22) | 0.28 |
| 18 Months | 292/311 | 48 (16.4) | 51 (16.4) | 1.00 (0.67, 1.49) | 0.99 | 1.01 (0.68, 1.50) | 0.97 |
| Either 12 or 18 months# | 236/248 | 61 (25.8) | 67 (27.0) | 0.96 (0.69, 1.33) | 0.79 | 0.96 (0.69, 1.33) | 0.81 |
| Special diet for food allergy | | | | | 0.97 | | 0.96 |
| 12 Months | 232/248 | 12 (5.2) | 13 (5.2) | 0.99 (0.42, 2.31) | 0.98 | 0.98 (0.42, 2.27) | 0.96 |
| 18 Months | 292/311 | 12 (4.1) | 13 (4.2) | 0.98 (0.42, 2.31) | 0.97 | 0.99 (0.42, 2.33) | 0.98 |
| Either 12 or 18 months# | 230/243 | 20 (8.7) | 17 (7.0) | 1.24 (0.62, 2.50) | 0.54 | 1.25 (0.62, 2.51) | 0.53 |

Non-imputed data presented. Abbreviations: DHA, docosahexaenoic acid; CI, confidence interval.
*Adjusted for GA at delivery and sex
Excluding missing data

TABLE 5

Hay fever data by subgroup

| | High-/Standard-DHA Diet, No. | High-DHA Diet, No. (%) | Standard-DHA Diet, No. (%) | Unadjusted Relative Risk (95% CI) | Unadjusted P value | Adjusted Relative Risk* (95% CI) | Adjusted P value |
|---|---|---|---|---|---|---|---|
| BIRTH WEIGHT < 1250 g | | | | | | | |
| 12 Months | 102/107 | 2 (2.0) | 6 (5.6) | 0.35 (0.07, 1.80) | 0.21 | 0.35 (0.07, 1.88) | 0.22 |
| 18 Months | 133/141 | 4 (3.0) | 5 (3.5) | 0.85 (0.23, 3.08) | 0.80 | 0.85 (0.23, 3.13) | 0.81 |
| Either 12 or 18 months# | 101/106 | 5 (5.0) | 10 (9.4) | 0.52 (0.18, 1.53) | 0.24 | 0.52 (0.18, 1.53) | 0.24 |
| BIRTH WEIGHT ≥ 1250 g | | | | | | | |
| 12 Months | 130/142 | 3 (2.3) | 7 (4.9) | 0.47 (0.12, 1.77) | 0.26 | 0.47 (0.12, 1.76) | 0.26 |
| 18 Months | 159/170 | 3 (1.9) | 5 (2.9) | 0.64 (0.16, 2.64) | 0.54 | 0.64 (0.16, 2.62) | 0.54 |
| Either 12 or 18 months# | 130/138 | 3 (2.3) | 11 (8.0) | 0.29 (0.08, 1.01) | 0.05 | 0.29 (0.08, 1.02) | 0.05 |
| MALE INFANTS | | | | | | | |
| 12 Months | 126/139 | 1 (0.8) | 10 (7.2) | 0.11 (0.01, 0.87) | 0.04 | 0.11 (0.01, 0.85) | 0.03 |
| 18 Months | 155/168 | 2 (1.3) | 5 (3.0) | 0.43 (0.08, 2.41) | 0.34 | 0.43 (0.08, 2.41) | 0.34 |
| Either 12 or 18 months# | 125/137 | 2 (1.6) | 15 (10.9) | 0.15 (0.03, 0.64) | 0.01 | 0.15 (0.03, 0.64) | 0.01 |
| FEMALE INFANTS | | | | | | | |
| 12 Months | 106/110 | 4 (3.8) | 3 (2.7) | 1.38 (0.32, 6.05) | 0.67 | 1.42 (0.33, 6.16) | 0.64 |
| 18 Months | 137/143 | 5 (3.6) | 5 (3.5) | 1.04 (0.31, 3.52) | 0.94 | 1.05 (0.31, 3.56) | 0.93 |
| Either 12 or 18 months# | 106/107 | 6 (5.7) | 6 (5.6) | 1.01 (0.34, 3.03) | 0.99 | 1.04 (0.35, 3.13) | 0.94 |

Non-imputed data presented. Abbreviations: DHA, docosahexaenoic acid; CI, confidence interval.
*Adjusted for GA at delivery
Excluding missing data

What is claimed is:

1. A method for promoting the respiratory development of an infant or for reducing the incidence of respiratory distress or bronchopulmonary dysplasia in an infant, the method comprising administering to the infant an effective amount of DHA.

2. The method of claim 1 comprising administering to the infant DHA in an amount of at least about 30 mg/kg of body weight per day, at least 60 mg/kg of body weight per day, or at least about 90 mg/kg of body weight per day.

3. The method of claim 1, wherein the infant is a preterm infant.

4. The method of claim 3, wherein the infant is born prior to 33 weeks or 36 weeks gestation.

5. The method of claim 3, wherein the administration is continued until the infant reaches term corrected age.

6. The method of claim 1, wherein the infant is classified as small for gestational age.

7. The method of claim 1, wherein the infant has a birth weight of less than or equal to about 1250 g.

8. The method of claim 1, wherein the administration commences within about 24 hours of the birth of the infant, or at a time when the infant commences enteral feeding.

9. The method of claim 1, wherein the administration is enteral or parenteral administration.

10. The method of claim 1, wherein the DHA is administered to the infant in combination with one or more of the following: human milk, infant formula, human milk fortifier, a source of protein, and vitamins and/or minerals.

11. The method of claim 1, wherein the DHA is administered in the form of an emulsion.

12. The method of claim 1, wherein the DHA is administered to the infant at least once a day, at least three times a day or at least five times a day.

13. A method of promoting the respiratory development of an infant or reducing the incidence of respiratory distress and/or bronchopulmonary dysplasia in an infant, the method comprising:
(i) administering fatty acids including DHA to the infant's mother in an amount sufficient to provide a content of DHA in the breast milk of the infant's mother that is about 1% or more of the total fatty acids present in the breast milk, and
(ii) feeding the infant with breast milk following step (i).

14. The method of claim 13, wherein step (i) comprises administering fatty acids including DHA to the infant's mother in an amount and over a time period sufficient to provide a constant DHA content in the breast milk of the infant's mother that is about 1% or more of the total fatty acids present in the breast milk of the infant's mother.

15. The method of claim 13, wherein step (i) comprises administering fatty acids including DHA to the infant's mother on a daily basis, and wherein the daily dosage of DHA is greater than about 600 mg.

16. The method of claim 15, wherein step (i) comprises administering fatty acids including DHA to the infant's mother on a daily basis, and wherein the daily dosage of DHA is greater than about 800 mg.

17. The method of claim 16, wherein step (i) comprises administering fatty acids including DHA to the infant's mother on a daily basis, and wherein the daily dosage of DHA is about 900 mg or greater.

18. The method of claim 13, wherein the infant is a preterm infant.

19. The method of claim 13, wherein the infant is born prior to 33 weeks or 36 weeks gestation.

20. The method of claim 18, wherein the feeding is continued until the infant reaches term corrected age.

21. The method of claim 13, wherein the infant is classified as small for gestational age.

22. The method of claim 13, wherein the infant has a birth weight of less than or equal to about 1250 g.

23. The method of claim 13, wherein the feeding commences within about 24 hours of the birth of the infant.

24. The method of claim 13, wherein step (ii) is commenced about 1 week after commencement of step (i).

25. The method of claim 13, wherein the feeding is carried out at least once a day, at least three times a day or at least five times a day.

26. The method of claim 1, wherein the infant is a male.

27. The method of claim 13, wherein the infant is a male.

28. The method of claim 1, wherein the DHA is administered in a fatty acid composition, the DHA representing about 1% or more of the fatty acids.

29. The method of claim 28, wherein the DHA represents between about 1% and about 30% of the fatty acids.

30. The method of claim 13, wherein the infant's mother has been identified as being at risk of giving birth to the infant preterm, or at risk of giving birth to an infant that will be classified as small for gestational age.

31. A method for reducing the incidence of hay fever in an infant, the method comprising administering to the infant an effective amount of DHA.

32. A method for reducing the incidence of hay fever in an infant, comprising:
(i) administering fatty acids including DHA to the infant's mother in an amount sufficient to provide a content of DHA in the breast milk of the infant's mother that is about 1% more of the total fatty acids present in the breast milk, and
(ii) feeding the infant with breast milk following step (i).

* * * * *